United States Patent [19]

Grieco

[11] 4,284,794

[45] Aug. 18, 1981

[54] PROSTAGLANDIN DERIVATIVES

[75] Inventor: Paul A. Grieco, Pittsburgh, Pa.

[73] Assignee: University of Pittsburgh, Pittsburgh, Pa.

[21] Appl. No.: 750,956

[22] Filed: Dec. 16, 1976

[51] Int. Cl.$^3$ .......................................... C07C 177/00
[52] U.S. Cl. .................................. 560/121; 562/503; 424/305; 424/317
[58] Field of Search ...................... 260/408 D, 514 D; 560/121; 562/503

[56] References Cited

PUBLICATIONS

Wang et al., J.C.S. Chem. Comm. 1976, p. 468.

Primary Examiner—Robert Gerstl
Attorney, Agent, or Firm—Arnold B. Silverman

[57] ABSTRACT

Prostaglandins substituted at the 12 position with fluorine. These compounds are useful for a variety of pharmaceutical purposes including use as antifertility agents.

12 Claims, No Drawings

PROSTAGLANDIN DERIVATIVES

BACKGROUND OF THE INVENTION

1. Field of the Invention

This invention relates to 12 substituted prostaglandins that possess utility as luteolytic agents and for other pharmaceutical purposes.

2. Description of the Prior Art

Prostaglandins are natural hormones found in the human body. Various types of prostaglandins have been synthesized previously. Among the known properties of certain forms of prostaglandins are their capability to induce abortion in humans, their ability to function as regulators of muscle activity, lipid metabolism and certain other aspects of the reproductive process. It is also believed that they effect dilation of blood vessels, thereby reducing blood pressure. They are also believed to effect bronchial dilation. One of the problems with the natural substances has been the difficulty in separating the various biological activities in order to measure the effectiveness in respect of each independent property.

Fluorine has previously been substituted in the prostaglandin molecules. U.S. Pat. No. 3,833,640 discloses fluorine substitution near the end of the alkyl chain. See also U.S. Pat. Nos. 3,879,439; 3,969,378; 3,954,851 and 3,944,595. U.S. Pat. No. 3,935,241 discloses substitution of "$CH_2X$" at the 11 position, wherein X may be fluoro, chloro, bromo or others.

Methyl substitution in the nucleus of prostaglandins have been known. See U.S. Pat. Nos. 3,514,383; 3,935,241; 3,953,499 and 3,505,387. See also the article entitled "A Synthesis of 12-Substituted Prostaglandins" by Norio Nakamura and Kiyoshi Saki as published in the United Kingdom by Pergamon Press in Tetrahedron Letters No. 24, Pages 2049–2052 (1976), which reports the synthesis of 11-deoxy-12α-methyl prostaglandin $E_2$ and 11-deoxy-12α-hydroxymethyl prostaglandin $E_2$.

Non-nuclear methyl substitution has been disclosed in U.S. Pat. Nos. 3,728,382; 3,813,433 and 3,888,919.

Bromine substitution has been disclosed in U.S. Pat. Nos. 3,755,426; 3,912,725; 3,833,640; 3,935,241 and 3,944,595.

There has, therefore, been lacking a disclosure of any fluorine substituted in prostaglandins in the five-member ring nucleus. More specifically, there has been lacking a 12 substituted fluoro-prostaglandin, the method of making the same and the unique antifertility properties of the same.

SUMMARY OF THE INVENTION

The compounds of the present invention fill the above-described need by providing prostaglandin compounds or analogs substituted at the 12 position with fluorine. These compounds possess enhanced antifertility properties as compared with the natural hormone, as well as other useful properties. These compounds possess improved separation of activities as compared with the natural hormone and also exhibit low smooth muscle activity. More specifically, the present invention provides for such substitution at 12 in $PGF_{2\alpha}$, 15-epi $PGF_{2\alpha}$, $PGA_2$, 15-epi $PGA_2$ $PGE_2$ and 15-epi $PGE_2$.

It is an object of this invention to provide 12 substituted prostaglandin analogs possessing superior biological and pharmaceutical properties in respect of antifertility and other properties.

It is a further object of the present invention to provide such a series of analogs which may be economically and effectively fabricated and used.

It is a further object of this invention to provide processes for the production of such compounds.

These and other objects of the invention will be more fully understood from the following description of the invention.

DESCRIPTION OF THE PREFERRED EMBODIMENTS

The novel prostaglandin derivatives of the present invention are illustrated by the following formulae:

Prostaglandin Type $F_{2\alpha}$ has the following structure:

I 15-epi Prostaglandin Type $F_{2\alpha}$ has the following structure:

II

Prostaglandin Type $E_2$ has the following structure:

III 15-epi Prostaglandin Type $E_2$ has the following structure:

IV

Prostaglandin Type $A_2$ has the following structure:

V 15-epi Prostaglandin Type $A_2$ has the following structure:

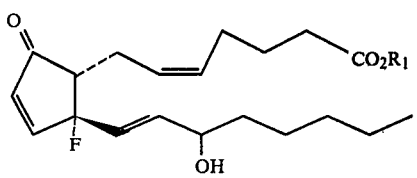

VI

In formula I-VI, $R_1$ is H or methyl.

While in a preferred form of the invention, the 12 substituted prostaglandins will be racemic compounds or optically inactive, it will be appreciated that the compounds may also be optically active.

EXAMPLE 1

An example of synthesis of 12-fluoro prostaglandin $F_{2\alpha}$ will now be considered.

concentrated sulfuric acid (20 drops) gave 55.3 g of diformate i. Oxidation of diformate i (55.3 g) in 900 ml of acetone at

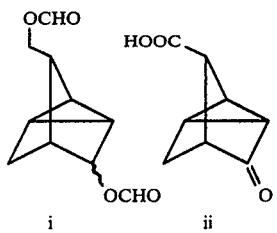

i    ii

0° C. with 553 ml of standard Jones reagent provided 27.2 g of keto acid ii. Treatment of 21.5 g ii with 225 ml of 48% hydrobromic acid in 225 ml of glacial acetic acid at reflux gave 28.1 g of bromo acid 1 ($R_2$=H,

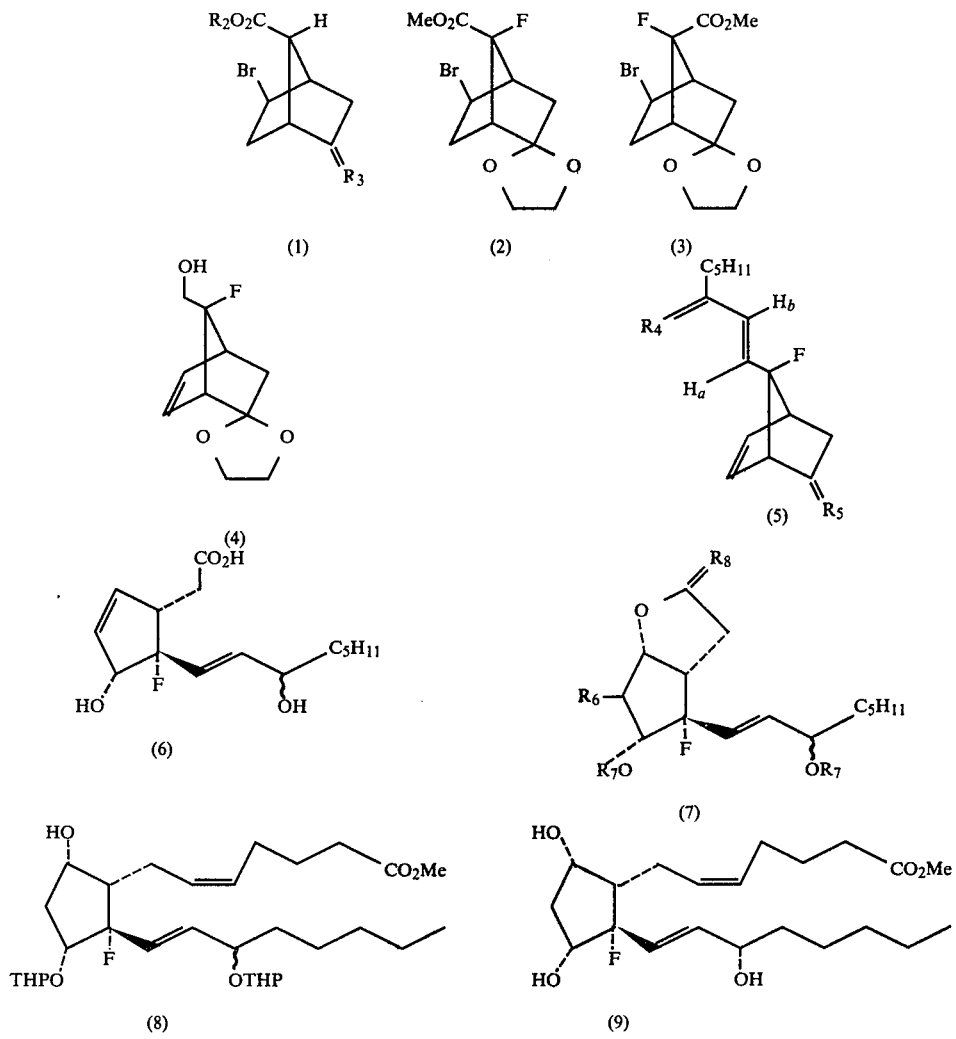

The process presented in this example will result in the synthesis of 12-fluoroprostaglandin $F_{2\alpha}$ methyl ester from norbornadiene, in a process which involves the fluorination of the enolate derived from an ester with perchloryl fluoride. In formula (1) there is shown a keto acid wherein $R_2$=H, and $R_3$=O. An ester may readily be synthesized from this keto acid by the following procedure from norbornadiene.

Reaction of 40.0 g of norbornadiene and 13.2 g of paraformaldehyde in formic acid (480 ml) containing $R_3$=O). Esterification of 1 ($R_2$=H, $R_3$=O) with ethereal diazomethane gave methyl ester of formula (1) wherein $R_2$=Me, and $R_3$=O. Ketalization of 16.1 g of keto ester 1 ($R_2$=Me, $R_3$=O) with 35.8 g of 2-methyl-2-ethyl-1,3-dioxolane in 150 ml of benzene containing 2.7 g of p-toluenesulfonic acid at 25° C. for 20 hours give 17.0 g of pure ketal ester of formula (1) wherein $R_2$=Me and $R_3$=—O(CH$_2$)$_2$O—. Fluorination of 4.66 g of ester 1 ($R_2$=Me, $R_3$=—O(CH$_2$)$_2$O—) via enolate formation [lithium disopropylamide, tetrahydrofuran, −78° C.] and slow addition of perchloryl fluoride (−40° C.) resulted in an 86% isolated yield of a pure mixture of the desired α-fluoro ester shown in formula (2) ($R_f$ 0.41) [hexane-ethyl acetate (4:1)] and the isomeric α-fluoro ester shown in formula (3) ($R_f$ 0.33 in a ratio of 1:1.). Chromatography on silica gel easily provided the α-fluoro ester of formula (2), which was reduced with lithium aluminum hydride in ether at 25° C. and dehydrobrominated with 1,5-diaza-bicyclo(5.4.- 0)undec-5-ene (10 equivalents) in refluxing toluene. An 84% yield of the pure alcohol shown in formula (4) M+200.0850 was obtained. As fluorination with perchloryl fluoride can be hazardous, safety precautions should be observed.

In situ Collins oxidation [chromium trioxide (3.75 g), pyridine (6.1 ml), methylene chloride (70 ml)] of 0.50 g of the compound of formula (4) in 2.0 ml of methylene chloride followed by condensation with the sodium derivative of dimethyl 2-oxoheptylphosphonate (0.55 g) in dry tetrahydrofuran (12 ml) at 50° C. for 22 hours produced the pure trans-enone shown in formula (5) ($R_4$=O, $R_5$=—O(CH$_2$)$_2$O—) [J(H$_a$-H$_b$) 16 Hz, J(H$_a$-F) 18 Hz] in 51% yield. Reduction (NaBH$_4$-EtOH at −20° C.) with subsequent deketalization (30% acetic acid (25° C.)) provided a 95% yield of the ketone represented by formula (5) when $R_4$=H, OH and $R_5$=O. Baeyer-Villiger oxidation of ketone 5($R_4$=H, OH; $R_5$=O) (369 mg) with 30% hydrogen peroxide (0.89 ml) and aqueous sodium hydroxide (143 mg in 3 ml of water) in aqueous methanol (5 ml of methanol, 2 ml of water) at 5° C. for 48 hours afforded the hydroxy acid of formula (6) in 75% yield. Iodolactonization of the hydroxy acid of formula (6) gave the iodolactone of formula (7) (84%) wherein $R_6$=I, $R_7$=H and $R_8$=O. The iodolactone (241 mg) upon treatment with azobisisobutyronitrile (15 mg) and tri-n-butyltin hydride (350 mg) in benzene (8 ml) at 53° C. gave a 70% yield of the compound illustrated in formula (7) wherein $R_6$=H, $R_7$=H and $R_8$=O. Treatment with dihydropyran and reduction with i-Bu$_2$AlH-toluene at −70° C. produced the hemiacetal (70%) which has the structure shown in formula (7) wherein $R_6$=H, $R_7$=THP and $R_8$=H,OH. Condensation with the Wittig reagent derived from Ph$_3$P$^+$CH$_2$(CH$_2$)$_3$CO$_2$HBr$^-$ and MeSOCH$_2^-$Na$^+$ gave an hydroxy carboxylic acid (70%) which was directly esterified with ethereal diazomethane. Removal of the tetrahydropyranyl (THP) groups of the compound shown in formula (8) under acidic conditions (acetic acid-water-THF(20:10:3), at 42° C., 4.5 hr) gave a ca.1:1 mixture of the ester shown in formula (9) and its C-15 epimer which were separated by column chromatography on silica gel.

The stereochemistry of intermediates discussed above was established by n.n.r. analysis utilizing the known dependents of $J_{HF}$ on dihedral angle and long-range proton fluorine coupling in rigid systems.

EXAMPLE 2

Examples of how to synthesize 12-fluoro PGE$_2$ and 12-fluoro PGA$_2$ will now be considered. The compound of formula (8) of Example 1 was subjected to Collins oxidation followed by hydrolysis of the tetrahydropyranyl protecting groups with aqueous acetic acid to generate 12-fluoro PGE$_2$. Treatment of the 12-fluoro PGE$_2$ under acidic conditions generated 12-fluoro PGA$_2$. A method of accomplishing the conversion to 12-fluoro PGA$_4$ involves treatment of ca. 35 μgms of 12-fluoro PGE$_2$ in 12 microliters of dioxane with 1 milliliter of a mixture of water-acetic acid-85% aqueous phosphoric acid (the mixture having a ratio of these constituents 10:3:2) at 70° C. for 1 hour. The major product yield of this procedure is 12-fluoro PGA$_2$.

The above-described examples have been descriptive of the methods of producing racemic or optically inactive compounds. In the event one were to desire to produce optically active isomers, one would merely resolve the compound of formula (1) in Example 1 wherein $R_2$ is H and $R_3$ is O.

The above-disclosed 12 substituted prostaglandins have been found to have properties that are effectively isolated. Also, the magnitude of antifertility properties is increased in respect of the natural hormone. The compounds which exhibit antifertility properties also exhibit low smooth muscle activity. In the context of the present disclosure, the term "antifertility" shall be deemed to include properties which result in prevention of conception, abortion and stimulation of birth prior to full development of the fetus.

Whereas particular embodiments of the invention have been described above for purposes of illustration, it will be evident to those skilled in the art that numerous variations of the details may be made without departing from the invention as defined in the appended claims.

What is claimed is:

1. An optically active compound of the formula:

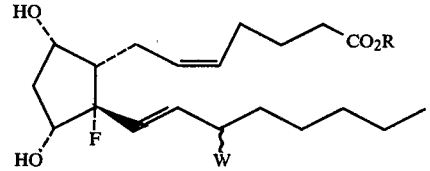

or a racemic compound of that formula and the mirror image thereof wherein R is H or CH$_3$ and W is

OH or

OH .

2. A compound according to claim 1 wherein said compound is racemic.

3. A compound according to claim 1 wherein R is CH$_3$.

4. A compound according to claim 1 wherein R is H.

5. A compound according to claim 1 wherein W is

OH .

6. A compound according to claim 1 wherein W is

OH .

7. An optically active compound of the formula:

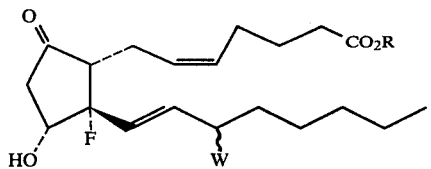

or a racemic compound of that formula and the mirror image thereof wherein R is H or CH₃ and W is

|
OH or

|
OH .

8. A compound according to claim 7 wherein said compound is racemic.

9. A compound according to claim 7 wherein R is CH₃.

10. A compound according to claim 7 wherein R is H.

11. A compound according to claim 7 wherein W is

|
OH .

12. A compound according to claim 7 wherein W is

|
OH .

* * * * *

UNITED STATES PATENT AND TRADEMARK OFFICE
CERTIFICATE OF CORRECTION

PATENT NO. : 4,284,794
DATED : August 18, 1981
INVENTOR(S) : PAUL A. GRIECO

It is certified that error appears in the above-identified patent and that said Letters Patent are hereby corrected as shown below:

Column 3, line 9, "formula" should read --formulae--.

Column 5, line 23, the word "trans-enone" should read --trans-enone--.

Column 6, line 1, "$PGA_A$" should read --$PGA_2$--.

Signed and Sealed this

Tenth Day of November 1981

[SEAL]

Attest:

Attesting Officer

GERALD J. MOSSINGHOFF

Commissioner of Patents and Trademarks